United States Patent
Goodhue, Jr. et al.

(10) Patent No.: US 6,248,697 B1
(45) Date of Patent: Jun. 19, 2001

(54) COMPOSITION AND METHOD FOR A DUAL-FUNCTION SOIL-GROUTING EXCAVATING OR BORING FLUID

(75) Inventors: K. Gifford Goodhue, Jr., Spring; Max M. Holmes, Laredo, both of TX (US); Clinton Scott Norman, Chattanooga; John M. Wilkerson, III, Hixson, both of TN (US)

(73) Assignee: KB Technologies, Ltd., Houston, TX (US)

( * ) Notice: Subject to any disclaimer, the term of this patent is extended or adjusted under 35 U.S.C. 154(b) by 0 days.

(21) Appl. No.: 09/023,150

(22) Filed: Feb. 12, 1998

Related U.S. Application Data
(60) Provisional application No. 60/037,712, filed on Feb. 12, 1997.

(51) Int. Cl.$^7$ .............................. C09K 7/02; C04B 12/04; E02D 5/18

(52) U.S. Cl. .................. 507/140; 106/633; 405/52; 405/263; 405/267; 507/110; 507/111; 507/118; 507/119; 507/120; 507/121; 507/122

(58) Field of Search ...................... 507/140, 118, 507/119, 120, 121, 122, 110, 111; 175/65, 72; 405/52, 263, 267; 106/633

(56) References Cited

U.S. PATENT DOCUMENTS

| | | | |
|---|---|---|---|
| Re. 29,716 | 8/1978 | Clampitt et al. | 175/65 |
| 1,815,876 | 7/1931 | Muller . | |
| 1,827,238 | 10/1931 | Joosten . | |
| 2,025,948 | 12/1935 | Jorgensen | 61/36 |
| 2,053,562 | 9/1936 | Jorgensen | 72/106 |
| 2,081,541 | 5/1937 | Joosten | 61/36 |
| 2,146,693 | 2/1939 | Vietti et al. | 255/1 |
| 2,165,823 | 7/1939 | Vietti et al. | 255/1 |
| 2,165,824 | 7/1939 | Vietti et al. | 255/1 |
| 2,205,609 | 6/1940 | Vail et al. | 255/1 |
| 2,239,647 | 4/1941 | Garrison | 255/1 |
| 2,437,387 | 3/1948 | Hodgson | 61/36 |
| 2,715,516 | 9/1955 | Bortnick | 260/86.1 |
| 2,798,053 | 7/1957 | Brown | 260/2.2 |
| 2,812,161 | 11/1957 | Mayhew | 255/1.8 |
| 3,040,820 | 6/1962 | Gallus | 175/66 |
| 3,652,497 | 3/1972 | Junas et al. | 260/47 |
| 3,657,175 | 4/1972 | Zimmerman et al. | 260/29.6 |
| 3,726,342 | 4/1973 | Rhudy et al. | 166/275 |
| 3,794,608 | 2/1974 | Evani et al. | 260/29.6 |
| 3,826,771 | 7/1974 | Anderson et al. | 260/29.6 |
| 3,878,151 | 4/1975 | Dachs et al. | 260/29.6 |
| 3,894,980 | 7/1975 | DeTommaso | 260/29.6 |
| 3,915,921 | 10/1975 | Schlatzer | 260/17.4 |
| 4,075,411 | 2/1978 | Dickstein | 560/224 |
| 4,076,628 | 2/1978 | Clampitt | 252/8.5 |
| 4,138,381 | 2/1979 | Chang et al. | 260/29.6 |
| 4,167,502 | 9/1979 | Lewis et al. | 260/29.6 |
| 4,268,641 | 5/1981 | Koenig et al. | 525/367 |
| 4,282,928 | 8/1981 | McDonald et al. | 166/274 |
| 4,293,427 | 10/1981 | Lucas et al. | 252/8.5 C |
| 4,338,239 | 7/1982 | Dammann | 524/549 |
| 4,374,738 | 2/1983 | Kelley | 252/8.5 C |
| 4,374,739 | 2/1983 | McLaughlin et al. | 252/8.55 R |
| 4,375,533 | 3/1983 | Park et al. | 526/193 |
| 4,384,096 | 5/1983 | Sonnabend | 526/313 |
| 4,421,902 | 12/1983 | Chang et al. | 526/317 |
| 4,470,463 * | 9/1984 | Holland | 166/293 |
| 4,473,190 | 9/1984 | Gagliardo | 239/456 |
| 4,500,436 | 2/1985 | Pabley | 252/8.5 |
| 4,506,062 | 3/1985 | Flesher et al. | 526/211 |
| 4,509,949 | 4/1985 | Huang et al. | 586/558 |
| 4,514,552 | 4/1985 | Shay et al. | 526/301 |
| 4,526,937 | 7/1985 | Hsu | 524/724 |
| 4,554,018 | 11/1985 | Allen | 106/20 |
| 4,554,298 | 11/1985 | Farrar et al. | 523/336 |
| 4,554,307 | 11/1985 | Farrar et al. | 524/425 |
| 4,596,838 * | 6/1986 | Andriechuk | 523/130 |
| 4,600,761 | 7/1986 | Ruffner et al. | 526/270 |
| 4,616,074 | 10/1986 | Ruffner | 526/318 |
| 4,656,205 | 4/1987 | Walker et al. | 523/201 |
| 4,660,645 | 4/1987 | Newlove et al. | 166/304 |
| 4,669,920 | 6/1987 | Dymond | 405/264 |
| 4,670,501 | 6/1987 | Dymond et al. | 524/458 |

(List continued on next page.)

FOREIGN PATENT DOCUMENTS

| | | | |
|---|---|---|---|
| 1191292 | 7/1985 | (CA) | C08K/9/02 |
| 2088344 | 10/1993 | (CA) | C09K/7/02 |
| 1332502 | 10/1994 | (CA) | C09K/7/02 |
| 0160427A2 | 11/1985 | (EP) | C07C/67/03 |
| 0165004A2 | 12/1985 | (EP) | A01C/3/00 |
| 0194857A2 | 9/1986 | (EP) | C09J/3/00 |
| 0200062 | 11/1986 | (EP) | C09K/7/02 |
| 0273210 | 7/1988 | (EP) | C09K/7/02 |
| 0634468A1 | 1/1995 | (EP) | C09K/7/02 |
| 2647463 | 11/1990 | (FR) | C09K/17/00 |
| 1517422 | 7/1978 | (GB) | C02B/1/20 |
| 2221904 | 2/1990 | (GB) | C07C/29/15 |
| 2221940A | 2/1990 | (GB) | C09K/7/02 |
| 2277759A | 9/1994 | (GB) | C09K/7/00 |

OTHER PUBLICATIONS

Burland, J.B. et al., Piling and Deep Foundations, Proceedings of the International Conference and Piling and Deep Foundations, London, May 15–18, 1989; A.A. Balkema/Rotterdam/Brookfield, 1989.

(List continued on next page.)

*Primary Examiner*—Philip Tucker
(74) *Attorney, Agent, or Firm*—Howrey, Simon, Arnold & White; Stephen H. Cagle; Carter J. White

(57) ABSTRACT

Compositions and methods useful in creating boreholes, tunnels and other excavations in unstable soils and earth formations, especially those composed partially or wholly of sand, gravel or other granular or permeable material are disclosed. The fluids include a polymer, and a soluble silicate ion source. The fluids of the invention, when used according to the methods of the invention, have unique dual functionality as excavating fluids and as earth-grouting or soil-hardening compositions.

20 Claims, No Drawings

U.S. PATENT DOCUMENTS

| | | | |
|---|---|---|---|
| 4,677,152 | 6/1987 | Allen et al. ............................ | 524/543 |
| 4,683,949 | 8/1987 | Sydansk et al. ...................... | 166/270 |
| 4,687,790 * | 8/1987 | Andriechuk .......................... | 523/130 |
| 4,696,698 * | 9/1987 | Harriett ................................. | 405/267 |
| 4,702,844 | 10/1987 | Flesher et al. ........................ | 210/733 |
| 4,722,397 | 2/1988 | Sydansk et al. ...................... | 166/295 |
| 4,724,906 | 2/1988 | Sydansk ................................ | 166/295 |
| 4,741,790 | 5/1988 | Hawe et al. ............................. | 156/71 |
| 4,743,698 | 5/1988 | Ruffner et al. ......................... | 549/478 |
| 4,744,418 | 5/1988 | Sydansk ................................ | 166/270 |
| 4,745,154 | 5/1988 | Ruffner ................................. | 524/801 |
| 4,777,200 | 10/1988 | Dymond et al. ...................... | 524/458 |
| 4,816,551 | 3/1989 | Oehler et al. ...................... | 528/295.3 |
| 4,835,206 | 5/1989 | Farrar et al. .......................... | 524/457 |
| 4,844,168 | 7/1989 | Sydansk ................................ | 166/270 |
| 4,892,916 | 1/1990 | Hawe et al. ........................... | 526/304 |
| 4,898,611 | 2/1990 | Gross ......................................... | 75/3 |
| 4,911,736 | 3/1990 | Huang et al. ............................ | 44/51 |
| 4,946,605 | 8/1990 | Farrar et al. ...................... | 252/8.514 |
| 4,980,434 | 12/1990 | Farrar et al. .......................... | 526/240 |
| 4,981,398 | 1/1991 | Field et al. ........................... | 405/264 |
| 4,984,933 * | 1/1991 | Annett et al. ......................... | 405/263 |
| 4,988,450 * | 1/1991 | Wingrave et al. .................... | 507/140 |
| 5,006,596 | 4/1991 | Chen et al. ............................ | 524/555 |
| 5,032,295 | 7/1991 | Matz et al. ........................... | 252/8.51 |
| 5,077,021 | 12/1991 | Polizzotti ............................... | 423/27 |
| 5,407,909 | 4/1995 | Goodhue et al. ..................... | 507/118 |
| 5,663,123 | 9/1997 | Goodhue et al. ..................... | 507/225 |

OTHER PUBLICATIONS

Chandra, Satish, *CRC Polymers in Concrete*, p. 18.

Clough, G. Wayne; "Silicate–Stabilized Sands"; *Journal of the Geotechnical Engineering Division*, Jan., 1979, pp. 65–83.

Gray, G.R., *Composition and Properties of Oil Well Drilling Fluids*, Fourth Edition, p. 560–563, 1980.

Hurley, Claude H.; "Sodium Silicate Stabilization of Soils: A Review of the Literature"; sponsored by Committee on Chemical Stabilization of Foundations; pp. 46–79, No Date Available.

Lambe, T. William; "Chemical Stabilization Can Make Construction Materials of Weak Soils"; *Engineering News Record*, Jul. 21, 1955, pp. 41–46.

Mainfort, R.C.; "A Laboratory Study of the Effectiveness of Various Chemicals as Soil Stabilizing Agents"; *Civil Aeronautics Administration Information and Statistics*, Oct., 1945.

Majano E. et al., *Effect of Mineral and Polymer Slurries on Perimeter Load Transfer in Drill Shafts*, A Report to ADSC, University of Houston, Jan. 1993.

Riedel, C. Martin; "Chemical Soil Solidification Work in Construction and Emergencies"; pp. 68–79, No Date Available.

Vail, D.Sc., James G.; *Soluble Silicates Their Properties and Uses, vol. 1: Chemistry;* American Chemical Society Monograph Series, Reinhold Publishing Corporation, 1952.

*Baroid Drilling Fluids Product Literature*, NL Baroid/NL Industries, Inc, No Date Available.

*Chemicals promote soil stabilization;* Chemical and Engineering, Oct. 17, 1966, pp. 80–82.

*EnviroTrench/GSP Product Literature*, Synthetic Polymers for Drilling and Trenching, Technical Information, Pelham, New York, No Date Available.

Foundation Engineering Handbook; Van Nostrand Reinhold, New York, 1991, pp. 326–330.

*Polymer Drilling Systems Product Literature*, PDSCO, El Dorado, Arkansas, No Date Available.

*Polymer Muds Find UK Unimpressed*, Ground Engineering, Nov. 1989.

*Slurry Specifications for Drilled Shafts*, Caltrans Specialists, No Date Available.

*Soil Stabilization with Liquid Sodium Silicate;* Occidental Chemical Corporation, May, 1994.

*Standard Specifications for the Construction of Drilled Piers*, ACI Committee 336, ACI 336.1–89., (1989).

*Standards and Specifications for the Foundation Drilling Industry*, ADSC, Revised 1991, Incorporating ACI 331.1–79.

Bol, G.M., The Effect of Various Polymers & Salts on Borehole & Cutting Stability in Water–Based Shale Drilling Fluids. Koninklijke/Shell E&P Laboratorium, IADC/SPE Conference 1986; IADC/SPE 14802.

Bruce, D.A. et al., *Structural Underpinning by Pinpiles.*, No Date Available.

Carnicom, W.M., *A Systems Approach for the Solution of Mud Problems*, NL Baroid/NL Industries, Inc., 1982.

Cernak, B., *The Time Effect Suspension of the Behavior of Piers*, Institute of Civil Engineering, Bratislava, CSSR., No Date Available.

Chesser, B.G., Design Considerations for an Inhibitive & Stable Water–Based Mud System, Milpark, Houston, Texas, IADC/SPE Conference 1986, IADC/SPE 14757.

Cooke, R.W., *Load Transfer from Bored, Clay–In–Situ Piles in London Clay*, 1979.

Crapps, D., *Design Construction, and Inspection of Drilled Shafts in Limerock and Limestone,* Prepared for 35th Annual Geotechnical Conference, University of Kansas, Mar. 7, 1986.

Day, P.W. et al., *Skin Friction of Underslurry Piles.*, No Date Available.

Eide, O. et al., *Special Application of Cast–in–Place Walls for Tunnels in Soft Clay in Oslo,* Norwegian Geotechnical Institute, Bonde & Co., Oslo, 1972.

Fearenside, G.R. et al., *The Skin Friction of Bored Piles Formed in Clay Under Bentonite,* Construction Industry Research and Information Association, London, No Date Available.

Felio, G.Y. et al., *A New Rod Shear Device for the Measurement of the Degradation of Soil–Pile Interfaces,* University of California at Los Angeles, Presented at 21st Annual OTC in Houston, Texas, May 14, 1989.

Fisk, J. & Perez, J., *Filtration Studies to Determine Filter Cake Compressibilities for Sun Oil's EZ–Mud Fluid,* NL Baroid/NL Petroleum Services, Inc., Fluids Research & Development Technical and Analytical Services/Support; EMB–4305; Jan. 29, 1988.

Fisk, J.V. et al., *Physical Properties of Drilling Fluids at High Temperatures and Pressures,* Baroid Drilling Fluids, SPE Drilling Engineering, Dec. 1989.

Fleming, C.N., *Moderate pH, Potassium, Polymer–Treated Mud Reduces Washout,* Chevron USA, Inc., IADC/SPE Conference 1986; IADC/SPE 14758.

Gale, R.S., *Filtration Theory with Special References to Sewage Sludges*, 1967.

Garrison, A.D. et al., *Dispersion of Clay and Shales by Fluid Motion,* Galveston Meeting, 1939.

Gray, G.R., *Drilling with Mud; Simple Tests Save Time and Money,* Baroid Division, NL Industries, Inc, No Date Available.

Gray, G.R., *Plan the Mud Program to Reduce Exploration Cost,* Mining Industry, Baroid Division, National Lead Co., Houston, Texas, No Date Available.

Gray, G.R., *Right Drilling Fluid Key to Efficient Operation,* Mining Industry, Baroid Division, NL Industries, Inc, No Date Available.

Guild, G.J., *Operating PHPA/NaCI Systems,* Amoco Production Company, Jan. 1990.

Hager, R., *Cast–In–Drilled–Hole–Piles in Adverse Soil Conditions,* State of California, Business and Transportation Agency, Department of Public Works, and Division of Highways Bridge Department, No Date Available.

Hagimoto, H. et al., *D.K. Shield Method,* Daho Construction Co. Ltd., Tokyo, Japan, 1990.

Holcombe, R.F. et al., *Subsidence of the Houston/Galveston Area,* McClelland Engineers, Spring, 1980.

Holden, J.C., *The Construction of Bored Piles in Weathered Sedimentary Rock,* Road Construction Authority of Virginia, May 1984.

Hooks, J. M. et al., *The Design & Construction of Diaphragm Walls in Western Europe 1979,* Supplement to 1980 World Survey of Current Research & Development on Roads & Road Transport, Dec. 1990.

Inoue, T. et al., *An Investigation of Shear Strength of Slurry Clay,* Japanese Society of Soil Mechanics and Foundation Engineering, Dec. 1990.

Janes, M. et al., *Pile Load Test Results Using the New Statnamic Method,* Berminghammer Corporation, McMaster University, No Date Available.

Janes, M., *Statnamic Load Test Results,* Comparative Pile Foundation Load Test Program, Texas A&M University, 1991.

Johnston, I.W., *New Developments in the Prediction of Side Resistance of Piles in Soft Rock,* Monash University, Melbourne, No Date Available.

Johnson, I.W. et al., *Side Resistance of Piles in Weak Rock,* Monash University, Melbourne, Victoria, Australia, 1992.

Kadaster, A.G. et al., *Field Application of PHPA Muds,* Amoco Production Co., Amoco Norway, Society of Petroleum Engineers Conference 1989, SPE 119531.

Kheng, H.Y., *Rheological and Physico–Chemical Properties of Palygorskite Clay and Anionic Polymer Slurries Used in Drilling Shaft Construction,* A Dissertation Presented to the Univ. Of Florida, 1989.

Kulhawy, F.H., *Drilled Shaft Foundations,* Cornell Univ., Ithaca, New York, 1989.

Lambe, T.W.,*The Structure of Compacted Clay,* Soil Mechanics and Foundations Division, May 1958.

Leyendecker, E.Q., *Drilling Fluids as Used with Drilled Shaft Construction,* Dresser Industries, Presented at the State Department of Highways and Public Transportation, Austin, Texas, 1984.

Liao, A., *Evaluation of Polymer–Bentonite Soil Admixtures as Hydraulic Barriers for Oilfield Waste Pits and Non–Oilfield Applications,* NL Baroid/NL Industries, Inc., 1988.

Liao, W.A. et al., *Absorption Characteristics of PHPA on Formation Solids,* Baroid Drilling Fluids, Inc., 1990 IADS/SPE Drilling Conference, Houston, Texas, Feb. 27–Mar. 2, 1990.

O'Neill, M. et al., *Effects of Mineral and Polymer Slurries on Side Load Transfer in Drilled Shafts,* University of Houston, Jan. 1992.

O'Neill, M. et al., *Effects of Stratigraphic and Construction Details on the Load Transfer Behavior of Drilled Shafts,* Transportation Research Board, 71st Annual Meeting, Jan. 12–16, 1992, Washington, D.C.

O'Neill, M.W., *Effects of Mineral and Polymer Slurries on Drilled Shafts,* Paper Presented to the Deep Foundation Institute, Chicago, IL, Oct. 8, 1991.

O'Neill, M.W., *Slide Load Transfer in Driven and Drilled Piles,* Mar. 1984.

Pells, P.J.N. et al., Bentonite Piles in Durban, Soil Mechanics and Foundation Engineering, Proceedings of the Sixth Regional Conference for Africa, Dubai, 1975.

Plank, J.P., Visualization of Fluid–Loss Polymers in Drilling Mud Filter Cakes, SKW Trostberg AG & F.A. Gossen, SKW Chemicals, Inc., Society of Petroleum Engineers Conference 1989; SPE 19534.

Reese, L.C. et al., *Bentonitic Slurry in Constructing Drilled Piers,* University of Texas, No Date Available.

Reese, L. C., *Drilled Piers in Rock,* 1989.

Rowe, P.W. et al., *Energy Components During the Triaxial Cell and Direct Shear Tests,* No Date Available.

Sliwinski, Z.J. et al., *Conditions for Effective and Bearing of Bored Cast–In–Situ Piles,* ICE, London, 1979.

Tamaro, G., *Slurry Wall Technical Course,* Resource Management Projects, Apr. 19 & 20, 1976.

Tan, M.J.C. et al., *Estimation of Side Resistance of Compressible Piles in a Softening Medium,* Australian Geomechanics, Oct. 1991.

Tan, T.S. et al., *Behavior of Clay Slurry,* Japanese Society of Soil Mechanics and Foundation Engineering, Dec. 1990.

Tan, T.S. et al., *Sedimentation of Clayey Slurry,* No Date Available.

Timmerhaus, P. et al., *Plant Design and Economics for Chemical Engineers,* University of Colorado, No Date Available.

Tucker K. et al., *The Effect of Bentonitic Slurry on Drilled Shafts,* Research Report 351–IF, Project 3–5–83–351, Center for Transportation Research, University of Texas at Austin, Jul. 1984.

Turner, J. et al., *Drained Uplift Capacity of Drilled Shafts Under Repeated Axial Loading,* No Date Available.

Williams, Jr., M., *Radial Filtration of Drilling Muds,* Galveston Meeting, Oct. 1939.

Wong, R.C.K. et al., *Design and Performance Evaluation of Vertical Shafts: Rational Shaft Design Method and Verification of Design Method,* University of Alberta, Canada, Jan. 20, 1988.+

*Basic Guidelines for Running NL Baroid's EZ–Mud Polymer System,* NL Baroid/NL Industries, Inc, No Date Available.

*Bencor Processes,* Bencor Corporation of America, 2315 Southwell Rd., Dallas, TX, 75229, No Date Available.

*Bentonite–Extended Muds (Ben–Ex),* N.L. Baroid/NL Industries, Inc, No Date Available.

*Bored Piles,* Les Pieux Fores, U.S. Dept. Of Transportation Report No. FHWA–TS–86–206, Apr. 1986.

*Cassion Load Test Results, Residual Treatment Facilities, Phase I, Deer Land, MA,* GZA GeoEnvironmental, Inc., New Upperton Falls, MA; Jun. 1992; File No. 12553.2.

*Clay Chemistry,* NL Baroid/NL Industries, Inc., Jun. 19, 1989.

*Drilling Fluids Products Cross Reference Chart,* NL Baroid/NL Industries, Inc, No Date Available.

*Drilling Specialties Company Product Literature,* Drilling Specialties Co., 1981.

*Excerpt from Specification for Foundations Contract, Stage II, West Gate Freeway,* Federation of Piling Specialists, No Date Available.

*Field Filter Cake Experiments,* No Date Available.

*Filtration Equations,* No Date Available.

*Formulation and Properties of "Standard" Muds for CST Fluids Optimization Tests,* NL Baroid/NL Industries, Inc.; Jan. 9, 1990.

*Grouts and Drilling Muds in Engineering Practice,* British National Society of the International Society of Soil Mechanics and Foundation Engineering at the Institution of Civil Engineers held in May 1963.

*Hyperfloc Polyacrylamides, Technical Information Bulletin,* Hychem Inc. 1989.

*Influence of the Boring Methods on the Behavior of Cast–In–Place Bored Piles,* No Date Available.

*Komatsu Product Literature,* Tokyo, Japan, No Date Available.

*Load Test Data BP London,* No Date Available.

*Manual of Drilling Fluids Technologies; Calculations, Charts, and Tables for Mud Engineering,* NL Baroid/NL Industries, Inc., 1985.

*Manual of Drilling Fluids Technology; Fundamental Characteristics of Drilling Fluids,* NL Baroid/NL Industries, Inc., 1985.

*Manual of Drilling Fluids Technology; Sources of Mud Problems,* NL Baroid/NL Industries, Inc., 1985.

*Polymer Soil Conditioners,* SNF Floerger, 1990.

*Report of Geotechnical Engineering Evaluation Load Test Program for Drilled Shaft Foundations,* Ellis and Associates, Jan. 7, 1985.

*Standard Specification for the Construction of Drilled Piers,* ACI Committee 336, American Concrete Institute, Detroit, Michigan, No Date Available.

\* cited by examiner

COMPOSITION AND METHOD FOR A DUAL-FUNCTION SOIL-GROUTING EXCAVATING OR BORING FLUID

This application claims priority of U.S. Provisional Application Ser. No. 60/037,712 filed Feb. 12, 1997.

FIELD OF THE INVENTION

This invention relates to fluids for use in boring and excavating operations. More specifically, this invention relates to earth-stabilization and earth-support fluids, their composition, and techniques for preparing, using, and maintaining them. The compositions and methods are useful in creating boreholes, tunnels and other excavations in unstable soils and earth formations, especially those composed partially or wholly of sand, gravel or other granular or permeable material. The fluids of the invention, when used according to the methods of the invention. have unique dual functionality as excavating fluids and as earth-grouting or soil-hardening compositions.

BACKGROUND

In earth boring and excavating for wells, deep foundations. tunnels and other geotechnical applications. fluids or muds have been used to hold open and maintain the stability of boreholes and excavations. These fluids or muds have used hydrostatic pressure and controlled interaction with the earth to accomplish their functions. The excavations have been kept full of the fluids or muds during the excavating or boring process, with or without circulation of the fluids.

Separately in processes for improving the cohesion and load-bearing properties of granular or unconsolidated soils and other unstable granular earth formations or materials. reactive compositions have been injected into and mixed with the soils to cause solidification or hardening of the soils. These reactive compositions have comprised silicates cementitious grouts and other materials. The application of these soil-improvement materials and techniques has been done as a prelude to excavating, drilling, tunneling, or pile-driving, in order to render the soils resistant enough to support deep excavations for things such as foundation systems such as bored piles, or to bear the weight of structures erected on pad-type foundations or spread footings. These processes whereby weak soils are prepared to receive excavations for things such as foundation systems or other geoconstruction elements are generally referred to as ground improvement.

In a typical sequence of events for the construction of structures on poor soil, ground improvement techniques are used, followed by excavating or drilling to create deep foundation elements such as diaphragm wall panels, barrettes, or bored piles. Frequently the excavations or borings are made with the help of a fluid or mud as described above. In this two-step process the weak soil is first strengthened by ground improvement techniques such as reactive silicate injection or mixing, then excavations are created in or through the strengthened soil with the help of an excavating fluid or drilling mud. Finally, reinforced concrete is formed in the excavations in order to create a competent deep construction system.

In the prior art, silicates and silicate-reactive compounds have been injected into or mixed with granular, rubberized or vugular earth formations, fills or other materials in advance of or during pauses in drilling or excavating, to strengthen or solidify the earth formations. Polymer-based fluids have been used for excavating and drilling, to support the walls of the excavations or wells. And silicates have been added to drilling muds in attempts to prevent heaving of shales. What is unknown in the prior art is the formulation and effective application of a single fluid which is both and at the same time a drilling mud or earth support fluid and a reactive, soil-permeating, silicate-based chemical-grouting ground-improvement or ground-solidification agent which is effective in the presence of unstable earth environments (e.g. sand).

The instant invention offers an improvement over the prior arts for both the stabilization of boreholes, earth excavations and the like; and ground improvement. An adaptation of the invention is useful during the preparation of guide-walls for diaphragm walls and the solidification of near-surface zones of loose soil.

DESCRIPTION OF THE INVENTION

The instant invention is a composition and method of application for a dual-purpose excavating and soil-strengthening fluid composed of: water; water-dispersible polymers; alkalies; optionally soil or earth solids; various forms of sodium silicate; and, optionally, sodium aluminate, calcium chloride, carbon dioxide and chlorine gas, citric, sulfamic or other acids and salts thereof salts, or other crosslinking or catalytic agent which assists in making the sodium silicate—slurry solution somewhat insoluble to totally insoluble. The fluid's multi-purpose nature is expressed in its functions as (1) an earth-support fluid as known in the prior art, and (2) a soil-strengthening fluid which functions in a manner similar to silicate "chemical grouts" known in the prior art (3) a weighting agent to increase the specific gravity of a slurry system. The novelty lies in the accomplishment of the earth support function (as performed by drilling muds, etc.) concurrently and in combination with the chemical grouting or ground improvement function (as previously performed by reactive silicate injection and/or soil mixing prior to excavating or boring).

The fluids of the invention are preferably based on aqueous dispersions of water-dispersible polymers, and may contain inorganic buffers, polycationic additives, soil or mineral solids and other materials as disclosed in the prior art and in U.S. Pat. No. 5,407,909 and U.S. Pat. No. 5,663,123 the contents of which are hereby incorporated herein by reference. In expressing the current invention, these prior-art fluids are modified by dosing with sodium silicate and, optionally, sodium aluminate. The silicate, by being present in the excavating fluid, permeates the weak or unstable layers of granular earth material or fills which are penetrated by the excavating or boring machinery. The silicate reacts with the naturally occurring soil components under excavation, along with any introduced crosslinking or catalytic agents. The degree of strengthening, increased cohesion, or hardening is developed by enhancing or preventing alteration of weak bonds among the granular earth material, or by forming a glasslike siliceous matrix within the soils present. This effect is achievable in granular formations and soils such as gravel and sand; in filled areas and irregular materials such as rubberized concrete and mixed fills in and around old foundation systems; in sand-bearing soils such as clayey sand, sandy clay, silty sand and sandy silt; and in other permeable, elastic, granular or partially-granular earth formations such as glacial tills. oolite, shell beds, vugular or fractured rocks, rock washes and decomposed rock materials.

Because the fluids of the invention are low-solids fluids based on polymers, the whole fluid, when formulated with lower concentrations of or without fluid loss control provisions or additives, is able to permeate sandy earth formations more freely than can bentonite-based fluids, which deposit a low-permeability cake on the face of the formation. The bentonite filter cake allows principally water to pass into the formation, leaving most of the colloidal or water thickening constituents of the fluid in the filter cake. The soil-permeation characteristics of polymer-based fluids facilitate the fluids' ground improvement functionality when silicates are present in the fluids, because the silicates (and optional aluminates) are carried by the permeating whole fluid into the pore system of the formation surrounding the excavation. The fluids of the invention can also incorporate bentonite at up to about 3% wt./vol. Such polymer-extended, bentonite-containing fluids can exhibit soil-permeation characteristics sufficiently similar to pure polymer fluids that they can be useful in expressing the excavating fluid or composition of the invention, as well as the methods of the invention.

Fluids containing bentonite at concentrations greater than about 3% can also be used to express a method, if not a composition, of the invention. When bentonite-based fluids or other fluids based on finely-divided solids are dosed with the silicates, hydroxides and optional aluminates of the invention and used to drill or excavate the weak, loose or unconsolidated permeable earth formations discussed herein, the silicate-bearing filtrate from these fluids can permeate the formations and strengthen them by the mechanisms discussed.

The time required for the silicate to react with and significantly increase the stability of the earth formation is sufficiently short as to be useful to the excavator or driller to improve the efficiency of the excavating process or allow for the continuation of excavation in the absence of traditional soil stabilization pre-treatments such as grouting or post-treatments such as backfilling with earth, lean mix, or concrete. This improvement not only significantly impacts the logistics of excavating unstable soil, but reduces the overall cost of the excavation process.

This differs from classical methods of soil stabilization (ground improvement) wherein silicate compounds and usually calcium bearing agents and other compounds were separately injected into the ground with specially-designed equipment to stabilize the earth formation prior to attempting excavation or other steps in the geoconstruction process. This process of ground improvement is currently practiced prior to beginning many types of boring, excavating or geoconstruction. Until now it was always assumed that the soil needed to be stabilized prior to excavation, to make it excavable. In the excavation and construction of structures such as tunnels, barrettes, bored piles and slurry walls, the prior step of ground improvement may now be eliminated in many cases through the use of the present invention. The invention allows the direct excavation and simultaneous strengthening of unstable, low cohesion or weak zones or areas. The invention is thus useful and cost-beneficial to the industry.

This invention provides a novel method of delivery of a ground-improvement system in a practical and especially efficient manner that incorporates ground improvement into the process of excavating or boring. The invention adds strength to a freshly-excavated area that will last long enough to keep its shape through the completion of concrete placement (or the placing of casing or other downhole components, in the case of wells). It is compatible with polymer fluid systems currently in use in the industry, as well as with fluids based on bentonite and other finely-divided solids. One of the main uses of the invention is in bringing about adequate stability to running sands and loose earth layers typically containing mineral materials in an unstable mixture that is capable of sloughing or collapsing into the freshly cut or drilled areas.

This invention comprises the addition of about 0.1% to about 50.0% by weight of sodium silicate to the drilling/excavating fluid, using any of the commercially available forms of the chemical. The higher ratios of silicon dioxide to sodium oxide are preferred due to economy and utility.

The silicate most commonly employed in the treatment of building materials is a solution with a silica:alkali ratio of about 3.22 and is sold at a density of about 41 degrees B at about 68° F. or a specific gravity of about 1.39 to about 138. Such a product is known to be Grade N® from Philadelphia Quartz Company or Grade 40® from Oxychem. Inc. of New York. Illustrative commercially available silicate solutions and their composition are given below in Table 1.

TABLE 1

| Producer | Product Name | Wt. Ratio $SiO_2/Na_2O$ | % $Na_2O$ | % $SiO_2$ | Density @ 68° F. (20° C.) °Be' | lb/gal | g/cm$^3$ | Viscosity Centipoises |
|---|---|---|---|---|---|---|---|---|
| PQ | STIXSO ® RR | 3.25 | 9.2 | 30.0 | 42.7 | 11.8 | 1.41 | 830 |
| PQ | N ® | 3.22 | 8.9 | 28.7 | 41.0 | 11.6 | 1.38 | 180 |
| PQ | E ® | 3.22 | 8.6 | 27.7 | 40.0 | 11.5 | 1.37 | 100 |
| PQ | O ® | 3.22 | 9.1 | 29.5 | 42.2 | 11.8 | 1.41 | 400 |
| PQ | K ® | 2.88 | 11.0 | 31.7 | 47.0 | 12.3 | 1.47 | 960 |
| PQ | M ® | 2.58 | 12.4 | 32.1 | 49.3 | 12.6 | 1.50 | 780 |
| PQ | STAR ® | 2.50 | 10.6 | 26.5 | 42.0 | 11.7 | 1.40 | 60 |
| PQ | RU ® | 2.40 | 13.8 | 33.2 | 52.0 | 13.0 | 1.55 | 2,100 |
| PQ | D ® | 2.00 | 14.7 | 29.4 | 50.5 | 12.8 | 1.53 | 400 |
| PQ | C ® | 2.00 | 18.0 | 36.0 | 59.3 | 14.1 | 1.68 | 70,000 |
| PQ | STARSO ® | 1.80 | 13.4 | 24.1 | 44.6 | 12.0 | 1.43 | 60 |
| OXY | 40 | 3.22 | 9.1 | 29.2 | 41.5 | 11.67 | — | 206 |
| OXY | 40 Clear | 3.22 | 9.1 | 29.2 | 41.5 | 11.67 | — | 206 |
| OXY | 42 | 3.22 | 9.3 | 30.0 | 42.5 | 11.78 | — | 385 |
| OXY | JW-25 | 2.54 | 10.6 | 26.9 | 42.0 | 11.73 | — | 63 |
| OXY | JW Clear | 2.54 | 10.6 | 26.9 | 42.0 | 11.73 | — | 63 |
| OXY | 47 | 2.84 | 11.2 | 31.9 | 47.0 | 12.33 | — | 688 |
| OXY | 49 FG | 2.58 | 12.4 | 32.1 | 49.0 | 12.58 | — | 633 |
| OXY | 50 | 2.00 | 14.7 | 29.4 | 50.0 | 12.71 | — | 336 |

TABLE 1-continued

| Producer | Product Name | Wt. Ratio SiO$_2$/Na$_2$O | % Na$_2$O | % SiO$_2$ | Density @ 68° F. (20° C.) °Be' | lb/gal | g/cm$^3$ | Viscosity Centipoises |
|---|---|---|---|---|---|---|---|---|
| OXY | 52 | 2.40 | 13.9 | 33.4 | 52.0 | 12.98 | — | 1760 |
| OXY | WD-43 | 1.80 | 13.1 | 23.6 | 43.8 | 11.84 | — | 69 |

Information provided by PQ Corporation Typical Properties of Sodium Silicates Information and Occidental Chemical Corporation Literature There are four principal means of employing the sodium silicate in the practice of the invention. These, for purposes of explanation, are herein referred to as: (1) "Dilute Neat"; (2) "Concentrated Neat", (3) "Concentrated Accelerated", and (4) "Dilute Accelerated".

"Dilute Neat" denotes the addition of sodium silicate in relatively small concentrations (about 0.1% to about 10% by weight) to part or all of the volume of the fluid in use. The silicate acts as an additive to the system, and the silicate-treated excavating or boring fluid permeates the earth formation adjacent to the excavation in proportion to the conductivity of the formation to the fluid at the extant hydrostatic pressure differential. Silicate addition enhances the excavating or boring fluid's characteristics by developing a concentration gradient that increases the rate of fluid mobility into the surface walls of the excavation. The fluid can be any of the polymer-based or polymer-extended fluids known to those skilled in the art, with the added requirement that the fluid pH be maintained in the alkaline range of about 9 to about 13. The natural acidity or buffering capacity of the soil ideally causes a drop in pH of the permeating fluid, causing precipitation of silica onto the mineral surfaces and into the pore spaces of the formation adjacent to the borehole or excavation. Even in the absence of a sufficient drop in pH to precipitate silica, the silicate-bearing fluid can prevent destabilization of sandy formations. This is accomplished by a presumed action of preserving or reinforcing the weak hydrogen or silica-hydroxyl bonds between the grains of the formation.

The "Concentrated Neat" formulation and method consists of establishing a higher concentration (greater than about 10% by weight) of silicate in part or all of the volume of the fluid in use. This is typically accomplished by adding such a concentration of sodium silicate directly to that portion of the fluid which is, at the time of interest, in contact with the zone requiring stabilization. One method is to pour or deliver concentrated sodium silicate into the fluid in the open mouth of the excavation, and wait to allow time for the heavy silicate to sink to the lower portion of the excavation, thus establishing a "site-specific" concentration gradient that delivers a suitably high dose of silicate in that portion of the fluid which is involved in cutting into the unstable formation. Other methods of selectively delivering high doses ("slugs") of silicate to portions of the fluid column in a borehole or excavation are known to those skilled in the arts of excavating and drilling. (For example. in rotary-type well-drilling in which a circulating fluid is used, the conventional technique for "spotting" a liquid opposite a zone of interest may be used.) A Concentrated Neat application can also involve adding a suitable concentration of silicate to the entire volume of fluid in use, or boosting the silicate content of only a portion of a Dilute Neat system.

A "Concentrated Accelerated" application comprises the use of more than 10% by weight of silicate in all or a portion of the fluid in use, and further adding sodium aluminate or other analogous aluminate at up to and in excess of about 10% by weight to cause enhanced solidification of the soil/fluid mixture or of the fluid-permeated earth material. Such a mixture of suitable earth or mineral materials (such as sand, sandy soil, gravel, decomposed rock, granular mineral fills, rubberized or pulverized concrete, etc.) with water, alkali, polymers, sodium silicate and optionally sodium aluminate, will solidify to a stable mass in from a few minutes to several hours time. This Concentrated Accelerated system will require the presence of sodium aluminate from about 0.1% to greater than about 10.0% by weight of the fluid solids. The use of the Concentrated Accelerated system can allow excavation to continue almost without delay. Setting times for the Concentrated Accelerated system can be as little as about 30 seconds after the delivery and incorporation of the sodium aluminate into the portion of the silicate-treated fluid that is in contact with the zone of interest.

The fourth expression of the system, known herein as "Dilute Accelerated", comprises a fluid with a silicate content of less than about 10% by weight, dosed additionally with sodium or analogous aluminate at up to about 10% by weight. This dilute system is not expected to be as effective as the Concentrated Accelerated system due to a deficiency of silicate with which the aluminate can react. But it nonetheless may provide some useful functionality or benefit over the Dilute Neat system in some situations.

The instant invention can be summarized as: a composition and method of delivery of a soil-repairing or earth-strengthening excavating or boring fluid to a zone or layer where it is needed during the process of excavating or boring, to strengthen, harden or partially harden an incompetent, sloughing or running zone or layer of sand, sandy soil, or other granular mineral-bearing material in the earth. In order to differentiate the instant invention from previous efforts in the well-drilling art to use silicate-treated drilling fluids to stabilize shales, it can be specified that the instant invention is useful in earth formations or other zones of mineral-bearing materials found in the earth which are significantly permeable (permeability greater than about 100 millidarcies) and of relatively low compaction. That is to say, a significant portion by weight of the subject earth materials or formations has a grain size larger than about 20 micrometers (silt), and probably also a significant portion has a grain size larger than about 70 micrometers (sand), and compaction less than about 50 blows per foot, standard penetration, NPT. The invention is also expected to be useful in stabilizing weak or poorly-cemented sandy formations when a significant portion by weight of the subject earth materials or formations has a grain size larger than about 70 micrometers, with compaction higher than about 50 blows per foot, as might occur in well-drilling operation.

At the conclusion of concrete placement the final returned fluid of this invention from an excavation and also during the course of drilling a loaded soil or fluids no longer needed and excess fluids may be utilized around a project site in the useful manner of spray application to control dust in dry seasons or in areas of high concern about dusts from the project site.

Additionally the polymer based fluids of this invention may be used to control erosion by distributing around the site to soak into surface soils to aid in at least a partial consolidation to minimize loose soil run off.

The method of delivery of an excavation composition or soil repair fluid to a zone of an excavation or borehole wherein the excavation composition or soil repair fluid contains silicate salts at concentrations of about 0.1% to about 30% by weight of the total excavation composition, with alkaline hydroxides from about 0.01% to about 10.0% and aluminate salts from about 0.0% to about 30.0% of the fluid. The balance of the fluid is preferably water and small amounts of various water-dispersible polymers known to the industry (e.g. polyacrylamides, cellulosics, guars, starches, xanthan, et al), in addition finely-divided solids from the soils being excavated. The fluid may also be based on bentonite, other clays or finely-divided solids (e.g. hematite, barite, mixed clay, kaolin, calcium carbonate), or a combination of bentonite and polymers or other finely-divided solids and polymers.

Such a composition, when used in the excavation, drilling or treatment by permeation of incompetent, sloughing or running zones or layers of sand, sandy soil, sea shells, gravel, decomposed rock or concrete, or other granular mineral-bearing material in the earth, will constitute the delivery of a soil stabilization system for the purposes of this invention to enable the strengthening of the earth formation or material immediately surrounding or adjacent to the excavation or borehole. This fluid system allows stabilization or the solidification of incompetent or sloughing granular earth or mineral material to enable further drilling or excavating followed by such processes as in-situ formation of concrete foundation elements or the completion of wells in previously unconsolidated sands and soils. The silicates, hydroxides and aluminates are preferred to be in the sodium forms, but potassium, ammonium, and others such as magnesium, iron and calcium are useful.

One advantage of this instant invention is the ability to stabilize extremely weak zones without the use of cementitious mixtures based on portland cement or other calcium- or magnesium-bearing compounds (e.g. gypsum cement), which may take longer to set and which can contaminate drilling or excavating fluids with calcium or other divalent cations during subsequent re-excavation or drilling operations. Calcium contamination can damage most types of drilling or excavating fluids, resulting in increased cost and time expenditure to remedy the effects of such contamination. The system described in the instant invention can be formulated entirely without calcium or other divalent cations.

Given the above, one illustrative embodiment of the present invention is an excavation fluid composition useful for enlarging a cavity in the earth. The excavation fluid includes a synthetic polymer and sodium silicate. The composition is formulated so as to enable the fluid in contact with unstable or sandy soils in the selected areas of the excavation to react and form silicate-based derivatives with lesser solubility and movement. This formulation thereby improves soil stability at the excavation wall and enables the excavation of the earthen cavity to continue without the dangers of sloughing or caving in. In an alternative illustrative embodiment of this excavation fluid an aluminate salt is included which increases the speed of reaction of excavation fluid composition with the unstable and sandy soils. In yet another illustrative embodiment of this excavation fluid the composition further includes an alkalinity source. Exemplary alkalinity sources include the sodium and potassium salts of hydroxide and combinations thereof. Preferably the alkalinity source is present from about 0.01% to about 10.0% by weight of the excavation fluid. In yet another illustrative embodiment, the excavation fluid composition the synthetic polymer comprises one or more monomers selected from: acrylamide, methacrylamide, acrylic acid, methacrylic acid, maleic acid, fumaric acid; maleic anhydride, methacrylic anhydride, itaconic acid, acrylic acid dimer(BCEA), M-isopropenylbenzyl dimethyl isocyanate and the nonionic associative monomer derivatives, esters or urethane, so produced containing nonionic surfactant starting materials prepared from ethylene oxide and/or, propylene oxide and/or, butylene oxide and/or $C_1$ to $C_{20}$ alkyl alcohols and/or $C_8$ to $C_{12}$ alkyl phenols; itaconic acid, vinylsulfonic acid, styrene sulfonic acid, 2-acrylamido-2-methylpropane sulfonic acid, methallylsulfonic acid, vinyl acetic acid, 4-methylpentenoic acid, allylacetic acid, B-hydroxyethylacrylate, x-haloacrylic acid; M-isopropenylbenzyl dimethyl isocyanate and its nonionic derivatives prepared from alkyl alcohols; methylenebisacrylamide, N-methylol acrylamide, triallyl cyanurate, vinyl crotonate, divinylbenzene, allyl methacrylate; acrylic acid esters of sucrose, hexallyl sucrose, trimethylolpropane triacrylate, ethylene glycol diacrylate, diethylene glycol diacrylate, ethylene glycol dimethacrylate, and the like; methacrylic anhydride esters or maleic anhydride esters of sucrose, sorbitol, sorbitol esters with fatty acids; guar gum, starch, ethylated starch, oxidized starch, starch fatty acid esters, dodecylsuccinic anhydride modified starch. agar gum, xanthan gum, arabic gum or galacto-mannin derivatives prepared from methacrylic anhydride or maleic anhydride or M-isopropenylbenzyl dimethyl isocyanate resulting in hybrid monomers; vinyl acetate, N-vinyl formamide, N-vinyl acetamide, N-vinyl pyrolidone, styrene, butadiene, isoprene, chloro-butadiene, vinyl chloride. vinylidene chloride, $C_1$ to $C_{20}$ acrylate and methacrylate esters; methacryloxyethyl dimethylamine, methacrylamido propyl dimethylamine, dimethyl diallyl ammonium chloride, diethyl diallyl ammonium chloride, and their methyl sulfate and methyl chloride derivatives and water soluble or dispersible salts and combinations thereof. In a preferred illustrative embodiment the excavation fluid includes a synthetic polymer, sodium silicate that is about 0.1% to about 50.0% of the fluid composition, sodium hydroxide that is about 0.01% to about 10.0% of the fluid composition and sodium aluminate that is about 0.0% to about 30.0% of the fluid composition.

Yet another illustrative embodiment of the compositions of the present invention includes an anhydrous acid solidification mixture including: a structure material used to provide stability, strength, support, foundation, or volume to the solidification mixture and being selected from: sands, soils, clays, pebbles, cobbles, marble, granite, stones, gravel, rocks, bentonite, cement, polymer fibers, sandstone and combinations thereof, a polymer component; an accelerator compound selected from chemicals capable of producing carbon dioxide in acidic environments, chemicals capable of producing chlorine gas in acidic conditions, sodium aluminate, inorganic chloride salts, inorganic sulfate and inorganic sulfite salts; an acidic component selected from solid chemicals that gives $H^+$ in aqueous solutions; and a silicate component selected from sodium orthosilicate, sesquisilicate, metasilicate, disilicate and combinations thereof. In one preferred illustrative embodiment the accelerator compound is selected from the group consisting of potassium and sodium salts of hydrogen carbonate, potassium and sodium salts of carbonate, sodium and potassium hypochlorite, sodium aluminate, and combinations thereof, and wherein said acidic components is selected from the group consisting of citric acid, the salts of citric acid, sulamic acid, and combinations thereof.

A further illustrative composition contemplated herein is an anhydrous alkali solidification mixture. Like the previous acid solidification mixture, the alkali solidification mixture includes a structure material used to provide stability, strength, support, foundation, or volume to the solidification mixture and being selected from: sands, soils, clays, pebbles, cobbles, marble, granite, stones, gravel, rocks, bentonite, cement, polymer fibers, sandstone and combinations thereof. The composition further includes a polymer component; an accelerator compound, said accelerator compound being selected from sodium aluminate, all inorganic chloride salts, all inorganic sulfate or sulfite salts; a basic component, said basic component being selected from potassium or sodium hydroxide, the sodium or potassium salts of hydrogen carbonate, and carbonate, or any basic salt or solid chemicals that give $OH^-$ in aqueous solutions; and a silicate component said silicate component being selected from sodium orthosilicate, sesquisilicate, metasilicate, disilicate and combinations thereof.

Both the acid and the alkali solidification mixture described above may be used to stabilize an area under excavation by auger, drill, bucket, clam-shell, continuous cutter, grab and the like that is in the process of preparing a cavity by adding the solidification mixture into a bentonite or polymer based excavation composition with a silicate source present during the process of excavation.

The present invention also contemplates and encompasses the methods of using the fluids described herein in the stabilization of earth excavations. Thus, the present invention is contemplated to include a method of stabilizing the wall of an earthen excavation, the method including placing in said earthen excavation a digging fluid comprising a polymer and sodium silicate, the digging fluid composition is formulated so as to enable the fluid in contact with unstable or sandy soils in the selected areas of the excavation to react and form silicate-based derivatives with lesser solubility, and movement and thus improve soil stability at the excavation wall.

The contemplated methods of the present invention also include an improved method of stabilizing an earth excavation the earth excavation having within it a digging fluid, the digging fluid including water and a polymer. The improvement includes adding a soluble silicate ion source, a soluble hydroxide ion source, and optionally a soluble aluminate ion source to the digging fluid in concentrations sufficient to stabilize said earth excavation. In one preferred embodiment the soluble silicate ion source is selected from the group consisting of the sodium orthosilicate, sesquisilicate, metasilicate, disilicate and combinations thereof. In another embodiment the soluble hydroxide ion source is selected from the group consisting of the sodium and potassium salts of hydroxide and combinations thereof. In another embodiment the soluble aluminate ion source is selected from the group consisting of sodium, ammonium, potassium, salts of aluminate and combinations thereof. In another embodiment the source of soluble silicate ion is added prior to the addition of the source of soluble aluminate ion.

The methods of the present invention also encompass methods of using the above disclosed compositions to control erosion and dust by aiding in the consolidation of surface soils by the application to the surface soil. In one such embodiment a liquid as described above is applied and in another a dry powder is spread on the soil. This may also be used to control mud or to solidify ground that is to soft to otherwise work. Such applications will be apparent to one of skill in the art.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLE 1

In extremely wet sand in a backfilled lagoon in a coastal region in Asia, the normal digging of drilled shaft foundations for a high rise residential development was undertaken.

The 0.8 meter diameter digging bucket was used and the excavated walls were not considered stable enough to insure an adequate time frame for the placement of reinforcing steel and concrete. The contractor first elevated the casing by 1.5 meters. Approximately 2 meters above the water table was estimated. The casing was kept full of a polymer based fluid at all times. The hole was experiencing modest sloughing at 16 to 28 meters of depth.

At 28 meters onward, a stable marine clay was encountered. At the toe of the hole at 37 meters the friction pile was at full depth. The fluid used was at an adjusted pH of 10–12 with a SlurryPro® CDP and SlurryPro® MPA system from KB Technologies Ltd. of Chattanooga, Tenn. in use. The CDP polymer was used at 1.1 kilograms per cubic meter of fluid and the MPA was used at 0.01 kilograms per cubic meter of fluid. The Marsh Funnel Viscosity was maintained at 75 seconds/quart. The system was pronounced adequate under these severe running sand conditions with a concrete overbreak of approximately 25%. The area of this site was contaminated with a ruptured and abandoned sewer line with organic matter in the upper layers of the sandy zones.

EXAMPLE 2

At the same construction site as example 1 above, another excavation in the same area within 25 meters of the first example was drilled. Again 0.8 Meter diameter was excavated experiencing the same loose wet sand followed by marine clay and ending in a sandy clay at 37 meters down. The same fluid system as in example 1 was used as supplied by KB Technologies Ltd. of Chattanooga, Tenn. On this pile the addition of 2 drums of sodium silicate from a 40% solution was done at just below the casing at approximately 16 meters. This put a concentration of 4.1% sodium silicate into the fluid volume, w/w.

The resulting shift in the specific gravity of the excavation fluid system was an increase to 1.05 from an initial value of 1.01. The sandy deposits from the digging bucket were noticeably better formed with a "drier" appearance. They had a firmer feel and heaped up on the spoils pile in a more manageable way. The cleaning of the hole was improved with a reduction of sediment. The concrete overbreak was 19%. The addition of the sodium silicate seemed to have a chemical effect on the sandy zone and immediately facilitated a successful excavation beyond the weighting effect on the fluid itself.

EXAMPLE 3

Another example in the same extremely sandy are was performed where both sodium silicate and sodium aluminate were added to a very runny sandy zone at 16 to 30 meters below the surface. The same fluid was in use as in example 1 and 2 above.

The introduction of one drum of sodium silicate weighing 260 kilograms was placed at about 20 meters down into the drilling of this hole. This was allowed to mix for 5 minutes then a 25 kilogram bag of sodium aluminate was added to the top of the hole and drilling was continued after a 5 minute mix. The spoils from the bucket were noticeably drier and felt slightly warmer to the touch, An estimate of 3 degrees Centigrade rise in temperature was estimated for the material taken from the bucket. The hole was taken to full depth at 37 meters and cleaned in the usual way with about 0.4 meter of sediments. The concrete overbreak was 16%. This was considered an improvement.

EXAMPLE 4

At another site in Asia sodium silicate was used with a fluid like example 2 above. Here a 1.8 Meter pile was drilled for a railroad bridge. The pile was required to go through approximately 40 meters of totally decomposed granite and finished as a friction pile in a sandy clay at 45 meters depth.

During the drilling the t.d.g., totally decomposed granite, tends to stress relief itself. This makes for a small tightening of the hole and a need to keep small amounts of the sandy material from getting loose in the hole. The fluid level was maintained as high as practical, with a 1.5 meter elevated casing. The water table was approximately 6 meters down. The Marsh Funnel Viscosity for the excavation was held at 75 seconds/quart or higher at a pH of 12. Two drums of sodium silicate, 40%, were added at the 30 meter level. The casing for this hole was 21 meters. The specific gravity was increased 0.03 to 1.04. Of greater importance, the reactive material, sodium silicate, was delivered to the zone that most needed protection down to the 40 meter level. Beyond 40 meters a more clay bearing layer was encountered.

The resulting hole was drilled to depth and cleaned. The steel was placed and concrete overbreak was only 3%, typical for this sort of formation, The improvement to 0.7 meter of bottom sand sediment layer at the toe was an improvement from the 1 to 2 meters experienced normally.

EXAMPLE 5

The following procedure was followed to solidify a zone near the surface, after the removal of obstructions in preparation for the placement of a guide-wall for a diaphragm wall or slurry wall. The excavated area is filled with a mixture of sand, gravel, sea shell and sandy soil delivered to the site from a mixing system in water with a 12.0% sodium silicate content w/w added by the mix plant from a 40% grade of sodium silicate to create a premixed part one of a soil repair system. At the point of addition to the excavation, the slurry is approximately 75 to 85% solids content from the solid material. To this is co-added by a metering pump, a small stream of 6% sodium aluminate based solution from a commercially available source that has been enriched with sodium hydroxide by 4% of the formula weight of the excavation filling mixture; this is part two. The mixture is allowed to set for a period of one hour and then a solid sandstone material results suitable to allow the placement of a guide-wall.

This example is a replacement for a lean-mix concrete system that is produced from a calcium free formulation. The advantage is that when excavated the spoils will not harm the fluid integrity and the cost is justified since a damaged fluid will not result.

EXAMPLE 6

22.2 g of a 0.1% pH=11+SlurryPro CDP fluid was mixed with 181.4 g of blasting sand (Foster Dixiana). To this was added 60.0 g of QUIKRETE all purpose gravel and 56.0 g of 40% grade sodium silicate. The material was agitated to ensure complete mixing of components. A separate solution of 51.2 g of 45% grade sodium aluminate and 12.6 g of 50% grade sodium hydroxide was prepared and then added to the previous mixture with vigorous agitation for 15 seconds. Immediately the mixture was poured into a 3 inch round polystyrene cap. Before the material solidified a knife was used to level off the surface evenly with the edges of the cap. The newly formed mixture was unable to flow within 2 minutes of mixing. After one hour the mixture had solidified to a ridged beige solid. After 24 hour the solid "puck like" structure was removed from the cap. This material was subjected to a compression test and was able to support over 200 psi of applied force. Material calculated to be as 76.2% solids.

EXAMPLE 7

100.0 g of blasting sand, 1.0 g of finely ground SlurryPro CDP, 2.0 g citric acid, 3.8 g of sodium bicarbonate, and 0.65 g of 2-hydroxybenzoic acid were combined and mixed until a uniformly distributed dry mixture was observed. This material was used to provide two 53.5 g samples. A 50% w/w solution of 40% grade sodium silicate and Chattanooga City water was mixed. To a beaker was added 45.5 g of the 50% sodium silicate/water solution. Without any agitation or mixing, one dry mixture sample was added to this beaker. The second dry mixture sample was placed in a second beaker. To this beaker was added 53.0 g of the 50% sodium silicate/water solution. Both samples were completely submerged under the silicate/water solution. After 1 hour each sample was a thick sticky paste. While after 24 hours, each sample had solidified into a beige mass underneath the surface of the fluid.

EXAMPLE 8

100.0 g of blasting sand, 13.0 g of sodium aluminate powder, and 6.0 g of sodium hydroxide small beads were mixed until a uniform mixture observed. This material was split into two 59.5 g samples. One sample was added directly to 47.8 g of a 50% sodium silicate and water solution (see example #7). The second sample was added to 52.2 g of a 50% sodium silicate/water solution. Within 15 minutes each sample had formed a semi-solid mass. After 24 hours, each sample had developed further into a hardened mass.

EXAMPLE 9

A mixture of 181.4 g of blasting sand, 22.2 g of 0.1% pH=11+SlurryPro CDP fluid, and 56.0 g 40% grade sodium silicate were combined and allowed to sit for 24 hours. This mixture was added to a beaker filled with 0.1% pH=11+ SlurryPro CDP fluid and settled to the bottom of the beaker. A solution of 51.2 g of 45% grade sodium aluminate and 12.6 g of 50% grade sodium hydroxide was mixed. The sodium aluminate and sodium hydroxide solution was then injected into the lower portions of the sand mixture through a syringe. Within 10 minutes the sand layer had increased 20+° F. in temperature and a thick paste was forming around the area of injection. After 24 hours 90+% of the sand mixture was a combination of solid and gelled areas.

EXAMPLE 10

A beaker was filled with 0.1% pH=11+SlurryPro CDP fluid. To this was added 60.0 g of 40% grade sodium silicate which settled to the bottom of the beaker. A anhydrous mixture of 100 g blasting sand, 10g sodium hydroxide flake, and 15 g sodium aluminate powder were mixed until uniformity was observed. This anhydrous mixture was added to the beaker and settled on the bottom. After one hour the sand mixture was a gelled mass. After 24 hours the sand layer was a thick paste.

EXAMPLE 11

In a North East US city, a large cut and cover tunnel project requires that panels be installed near the original shoreline in areas of extreme fill and in an area where wood timbers from older foundations are numerous. The test panel selected is a secondary panel just north of a panel that had been difficult previously due to soft zones and wood piling obstructions. This panel was expected to be soft as well.

A photograph was taken of pretrenched area before fluid was added. Ground water was rushing in near bottom of pretench area. Fluid out of hose supply to fill trench was adjusted to 50 sec by Marsh Funnel Viscosity test at pH 10+. The initial excavation was mostly digging wood and rocks—no clay. The fluid contained tap water for make-up and 1.0 kilogram per ton SlurryPro®CDP, dry vinyl resin polymer, supplied by KB Technologies of Chattanooga, Tenn. The pH was adjusted with alkalis to pH 10–12. The fluid level in the excavation guide wall was holding but the spoils were very soupy in nature and poorly shaped. Inbound fluid at 48 seconds was measured. Gravel, marine shells and some marine clay were in the spoils. SlurryPro CDP was then added at the hole in dry form, ⅓ of a 44 pound bag of CDP, at the 17 feet depth. Now, 57 seconds in hole viscosity and pH 11+.

By observing a painted mark on the side of panel I-beam during 30 minute delay for chisel work to remove concrete on the panel I-beam, the fluid level was steady. No leaks at this time. The bucket is still bring up concrete and lean mixture. A top sample at 40 seconds/quart was measured due to concrete contamination. More CDP approx. ½ bag (22 pounds) is added.

The digging of concrete/lean mix at 20 feet continued. Incoming slurry was 55 seconds and pH 10. Added 1 gal of SlurryPro®MPA, a cationic polyamide resin supplied by KB Technologies, via a bag bomb to help seal the walls.

Viscosity now at 63 seconds. at 20 feet of depth. MFV in hole is 56 seconds and added another MPA bag bomb. Fluid level in the trench is holding steadily. At 33 feet mostly clay with gravel and sand we added another MPA bag bomb.

Continued to dig well. The hole was left open over the weekend.

To begin the next week, the crew began excavation, still chiseling—middle 34 feet with a 52 sec in hole viscosity. Evidence of a unstable layer was expected at 35 to 40 down.

Added Instafreeze® System to the panel: 3 drums—totaling 1980 pounds—Instafreeze additive (40% sodium silicate 3.22:1 SiO2: Na2O)—1 drum -660 pounds—Instafreeze C-2(sodium aluminate-40%) and 1 drum—660 pounds—of Protek 100, KOH, 45% alkalinity source) and continued to dig. At 40 feet all was in control and stable, the spoils were holding shape and no evidence of caving or heaving is noticed. Coden®—sonic logging device—Okay except for a small zig-zag at 30+ feet. The excavation has straight sides through the difficult zone. 53 seconds in the hole viscosity is maintained. Finally finished chiseling shape on Coden shows only a 1–2 foot nick in walls at sand layer. At 88 feet going and going to 90.5 feet into in the rock socket—some chisel damage up higher due to lean mix and concrete removal.

Hole finished: Concrete placement: 330 cubic yards for a 37.9% overbreak.

Collapse avoided—overall Okay. W=3.82 L 19.1 D=89 ft3=6493.62 48,572.26 gallons=239.27 yds3 The hole was done in three days of active operation and stayed open over a weekend holiday.

While the compositions and methods of this invention have been described in terms of preferred embodiments, it will be apparent to those of skill in the art that variations may be applied to the process described herein without departing from the concept, spirit and scope of the invention. All such similar substitutes and modifications apparent to those skilled in the art are deemed to be within the scope and concept of the invention as it is set out in the following claims.

What is claimed is:

1. An excavation fluid composition useful for enlarging a cavity in the earth comprising a synthetic polymer, sodium silicate, and an aluminate salt, said composition being formulated so as to enable the fluid in contact with unstable or sandy soils in the selected areas of the excavation to react and form silicate-based derivatives with lesser solubility, and movement and thus improve soil stability at the excavation wall and wherein, said aluminate salt increasing the speed of reaction of excavation fluid composition with the unstable and sandy soils.

2. The excavation fluid composition of claim 1 further comprising an alkalinity source, said alkalinity source being present from 0.01% to 10.0% by weight of the excavation fluid.

3. The excavation fluid composition of claim 1 wherein said synthetic polymer comprises one or more monomers selected from:

a. acrylamide, methacrylamide, acrylic acid, methacrylic acid, maleic acid, fumaric acid;

b. maleic anhydride, methacrytic anhydride, itaconic acid, acrylic acid dimer(BCEA), M-isopropenylbenzyl dimethyl isocyanate and the nonionic associative monomer derivatives, esters or urethane, so produced containing nonionic surfactant starting materials prepared from ethylene oxide and/or, propylene oxide and/or, butylene oxide and/or $C_1$ to $C_{20}$ alkyl alcohols and/or $C_8$ to $C_{12}$ alkyl phenols;

c. itaconic acid, vinylsulfonic acid, styrene sulfonic acid, 2-acrylamido-2-methylpropane sulfonic acid, methallylsulfonic acid, vinyl acetic acid, 4-methylpentenoic acid, allylacetic acid, B-hydroxyethylacrylate, x-haloacrylic acid;

d. M-isopropenylbenzyl dimethyl isocyanate and its nonionic derivatives prepared from alkyl alcohols;

e. methylenebisacrylamide, N-methylol acrylamide, triallyl cyanurate, vinyl crotonate, divinylbenzene, allyl methacrylate;

f. acrylic acid esters of sucrose, hexallyl sucrose, trimethylolpropane triacrylate, ethylene glycol diacrylate, diethylene glycol diacrylate, ethylene glycol dimethacrylate, and the like;

g. methacrylic anhydride esters or maleic anhydride esters of sucrose, sorbitol, sorbitol esters with fatty acids;

h. guar gum, starch, ethylated starch, oxidized starch, starch fatty acid esters, dodecylsuccinic anhydride modified starch, agar gum, xanthan gum, arabic gum or galacto-mannin derivatives prepared from methacrylic anhydride or maleic anhydride or M-isopropenylbenzyl dimethyl isocyanate resulting in hybrid monomers;

i. vinyl acetate, N-vinyl formamide, N-vinyl acetamide, N-vinyl pyrolidone, styrene, butadiene, isoprene, chloro-butadiene, vinyl chloride, vinylidene chloride, $C_1$ to $C_{20}$ acrylate and methacrylate esters;

j. methacryloxyethyl dimethylamine, methacrylamido propyl dimethylamine, dimethyl diallyl ammonium chloride, diethyl diallyl ammonium chloride, and their methyl sulfate and methyl chloride derivatives and water soluble or dispersible salts and combinations thereof.

4. method of stabilizing the wall of an earthen excavation, said method comprising:

placing in said earthen excavation a digging fluid, said digging fluid comprising a polymer, sodium silicate, and an aluminate salt, said composition being formulated so as to enable the fluid in contact with unstable or sandy soils in the selected areas of the excavation to react and form silicate-based derivatives with lesser solubility, and movement and thus improve soil stability at the excavation wall, and wherein said aluminate salt increasing the speed of reaction of excavation fluid composition with the unstable and sandy soils.

5. A method of stabilizing the wall of an earthen excavation, said method comprising:

placing in said earthen excavation a digging fluid, said digging fluid comprising a polymer, sodium silicate and an alkalinity source, said composition being formulated so as to enable the fluid in contact with unstable or sandy soils in the selected areas of the excavation to react and form silicate-based derivatives with lesser solubility, and movement and thus improve soil stability at the excavation wall, and wherein said alkalinity source being present from 0.01% to 10.0% by weight of the excavation fluid.

6. The method of claim 4 wherein said polymer comprises one or more monomers selected from:

a. acrylamide, methacrylamide, acrylic acid, methacrylic acid, maleic acid, fumaric acid;

b. maleic anhydride, methacrylic anhydride, itaconic acid, acrylic acid dimer(BCEA), M-isopropenylbenzyl dimethyl isocyanate and the nonionic associative monomer derivatives, esters or urethane, so produced containing nonionic surfactant starting materials prepared from ethylene oxide and/or, propylene oxide and/or, butylene oxide and/or $C_1$ to $C_{20}$ alkyl alcohols and/or $C_8$ to $C_{12}$ alkyl phenols;

c. itaconic acid, vinylsulfonic acid, styrene sulfonic acid, 2-acrylamido-2-methylpropane sulfonic acid, methallylsulfonic acid, vinyl acetic acid, 4-methylpentenoic acid, allylacelic acid, B-hydroxyethylacrylate, x-haloacrylic acid;

d. M-isopropenylbenzyl dimethyl isocyanate and its nonionic derivatives prepared from alkyl alcohols;

e. methylenebisacrylamide, N-methylol acrylamide, triallyl cyanurate, vinyl crotonate, divinylbenzene, allyl methacrylate;

f. acrylic acid esters of sucrose, hexallyl sucrose, trimethytolpropane triacrylate, ethylene glycol diacrylate, diethylene glycol diacrylate, ethylene glycol dimethacrylate, and the like;

g. methacrylic anhydride esters or maleic anhydride esters of sucrose, sorbitol, sorbitol esters with fatty acids;

h. guar gum, starch, ethylated starch, oxidized starch, starch fatty acid esters, dodecylsuccinic anhydride modified starch, agar gum, xanthan gum, arabic gum or galacto-mannin derivatives prepared from methacrylic anhydride or maleic anhydride or M-isopropenylbenzyl dimethyl isocyanate resulting in hybrid monomers;

i. vinyl acetate, N-vinyl formamide, N-vinyl acetamide, N-vinyl pyrolidone, styrene, butadiene, isoprene, chloro-butadiene, vinyl chloride, vinylidene chloride, $C_1$ to $C_{20}$ acrylate and methacrylate esters;

j. methacryloxyethyl dimethylamine, methacrylamido propyl dimethylamine, dimethyl diallyl ammonium chloride, diethyl diallyl ammonium chloride, and their methyl sulfate and methyl chloride derivatives and water soluble or dispersible salts and combinations thereof.

7. A method of stabilizing the wall of an earthen excavation, said method comprising:

placing in said earthen excavation a digging fluid, said digging fluid comprises:

a. a synthetic polymer, b. sodium silicate being 0.1% to 50.0% of the fluid composition c. sodium hydroxide being 0.01% to 10.0% of the fluid composition and d. sodium aluminate being 0.0% to 30.0% of the fluid composition, said composition being formulated so as to enable the fluid in contact with unstable or sandy soils in the selected areas of the excavation to react and form silicate-based derivatives with lesser solubility, and movement and thus improve soil stability at the excavation wall.

8. An improved method of stabilizing an earth excavation said earth excavation having within it a digging fluid, said digging fluid including water and a polymer, the improvement comprising adding a soluble silicate ion source, a soluble hydroxide ion source, and optionally soluble aluminate ion source to the digging fluid in concentrations sufficient to stabilize said earth excavation.

9. The improved method of claim 8 wherein the soluble silicate ion source is selected from the group consisting of the sodium orthosilicate, sesquisilicate, metasilicate, disilicate and combinations thereof.

10. The improved method of claim 8 wherein the soluble hydroxide ion source is selected from the group consisting of the sodium and potassium salts of hydroxide and combinations thereof.

11. The improved method of claim 8 wherein the soluble aluminate ion source is selected from the group consisting of sodium, ammonium, potassium, salts of aluminate and combinations thereof.

12. The improved method of claim 8 wherein the source of soluble silicate ion is added prior to the addition of the source of soluble aluminate ion.

13. An anhydrous acid solidification mixture comprising:

a. a structural material, said structural material being used to provide stability, strength, support, foundation, or volume to the solidification mixture and being selected from: sands, soils, clays, pebbles, cobbles, marble, granite, stones, gravel, rocks, bentonite, cement, polymer fibers, sandstone and combinations thereof, b. a polymer component;

c. an accelerator compound, wherein said accelerator compound is selected from the group consisting of potassium and sodium salts of hydrogen carbonate, potassium and sodium salts of carbonate, sodium and potassium hypochlorite, sodium aluminate, and combinations thereof, and an acidic component which is selected from the group consisting of citric acid, the salts of citric acid, sulamic acid, and combinations thereof: and e. a silicate component said silicate component being selected from sodium orthosilicate, sesquisilicate, metasilicate, disilicate and combinations thereof.

14. An anhydrous alkali solidification mixture comprising:

a. a structural material, said structural material being used to provide stability, strength, support, foundation, or volume to the solidification mixture and being selected from: sands, soils, clays, pebbles, cobbles, marble, granite, stones, gravel, rocks, bentonite, cement, polymer fibers, sandstone and combinations thereof, b. a polymer component;

c. an accelerator compound, said accelerator compound being selected from sodium aluminate, all inorganic chloride salts, all inorganic sulfate or sulfite salts;

d. a basic component, said basic component being selected from any basic salt or solid chemicals that give $OH^-$ in aqueous solutions; and e. a silicate component said silicate component being selected from sodium orthosilicate, sesquisilicate, metasilicate, disilicate and combinations thereof.

15. The method of using of an acidic solidification mixture as described in claim 13 to stabilize an area under excavation by auger, drill, bucket, clam-shell, continuous cutter, and grab that is in the process of preparing a cavity by adding said solidification mixture into a bentonite or polymer based excavation composition with a silicate source present during the process of excavation.

16. The method of using of an alkali solidification mixture as described in claim 14 to stabilize an area under excavation by auger, drill, bucket, clam-shell, continuous cutter, and grab that is in the process of preparing a cavity by adding said solidification mixture into bentonite or polymer based excavation composition, with a silicate source present during the process of excavation.

17. The method of using of an acidic solidification mixture as described in claim 13 to control erosion and dust by aiding in the consolidation of surface soils by application to the surface of this area of application on a construction site.

18. The method of using of an alkali solidification mixture as described in claim 14 to control erosion and dust by aiding in the consolidation of surface soils by application to the surface of this area of application on a construction site.

19. The method of using the excavation fluid composition of claim 1 to control erosion and dust by aiding in the consolidation of surface soils by application to the surface of this area of application on a construction site.

20. An excavation fluid composition useful for enlarging a cavity in the earth comprising:

a. a synthetic polymer;

b. sodium silicate being about 0.1% to about 50% of the fluid composition;

c. sodium hydroxide being about 0.01% to 10% of the fluid composition; and e. sodium aluminate being about 0.0% to 30% of the fluid composition, said composition being formulated so as to enable the fluid in contact with unstable or sandy soils in the selected areas of the excavation to react and form silicate-based derivatives with lesser solubility, and movement and thus improve soil stability at the excavation wall.

* * * * *